United States Patent
Choi et al.

(10) Patent No.: US 9,969,774 B2
(45) Date of Patent: May 15, 2018

(54) CELL PENETRATING PEPTIDE AND METHOD FOR DELIVERING BIOLOGICALLY ACTIVE SUBSTANCE USING SAME

(71) Applicant: IUCF-HYU (INDUSTRY-UNIVERSITY COOPERATION FOUNDATION HANYANG UNIVERSITY), Seoul (KR)

(72) Inventors: Je-Min Choi, Seoul (KR); Hyun-Jung Cho, Seoul (KR); Wonju Kim, Seoul (KR); Do-Hyun Kim, Seoul (KR); Jahyun Koo, Chungcheongnam-do (KR); Jung Ah Lee, Seoul (KR); Hong Gyun Lee, Seoul (KR); Sangho Lim, Seoul (KR)

(73) Assignee: IUCF-HYU (INDUSTRY-UNIVERSITY COOPERATION FOUNDATION HANYANG UNIVERSITY), Seoul (KR)

( * ) Notice: Subject to any disclaimer, the term of this patent is extended or adjusted under 35 U.S.C. 154(b) by 0 days. days.

(21) Appl. No.: 15/124,764

(22) PCT Filed: Mar. 10, 2015

(86) PCT No.: PCT/KR2015/002305
§ 371 (c)(1),
(2) Date: Nov. 10, 2016

(87) PCT Pub. No.: WO2015/137705
PCT Pub. Date: Sep. 17, 2015

(65) Prior Publication Data
US 2017/0057997 A1    Mar. 2, 2017

(30) Foreign Application Priority Data
Mar. 10, 2014    (KR) ........................ 10-2014-0027918

(51) Int. Cl.
| | |
|---|---|
| *A61K 38/00* | (2006.01) |
| *A61K 38/03* | (2006.01) |
| *A61K 38/08* | (2006.01) |
| *A61K 38/10* | (2006.01) |
| *A61K 48/00* | (2006.01) |
| *C07K 7/00* | (2006.01) |
| *C07K 7/06* | (2006.01) |
| *C07K 7/08* | (2006.01) |
| *C07K 14/435* | (2006.01) |

(52) U.S. Cl.
CPC ............ *C07K 7/06* (2013.01); *A61K 48/0075* (2013.01); *C07K 14/43595* (2013.01); *A61K 38/00* (2013.01); *C07K 2319/10* (2013.01); *C07K 2319/60* (2013.01)

(58) Field of Classification Search
CPC ........ A61K 38/00; A61K 38/03; A61K 38/08; A61K 38/10; A61K 48/00; C07K 14/43595; C07K 2319/00; C07K 2319/10; C07K 2319/60; C07K 7/06; C07K 7/00; C07K 7/08
USPC ................ 514/21.5, 21.6; 530/300, 327, 328
See application file for complete search history.

(56) References Cited

U.S. PATENT DOCUMENTS

| | | | |
|---|---|---|---|
| 2005/0196754 A1* | 9/2005 | Drmanac | C07K 14/8107 435/6.11 |
| 2007/0129305 A1 | 6/2007 | Divita et al. | |
| 2009/0305900 A1* | 12/2009 | Belouchi | C12Q 1/6883 506/7 |

FOREIGN PATENT DOCUMENTS

| | | |
|---|---|---|
| EP | 2090584 | 8/2009 |
| KR | 1020140010879 | 1/2014 |
| WO | 2012033272 | 3/2012 |
| WO | 2013160895 | 10/2013 |

OTHER PUBLICATIONS

UniProt L5KZJ6, pp. 1-4. Integrated into UniProtKB/TrEMBL Mar. 6, 2013.*
Joliot, et al., "Transduction peptides: from technology to physiology", Nature Cell Biology, vol. 6, No. 3, Mar. 2004.
Mogi, et al., "Elisa for Rankl-Opg Complex in Mouse Sera", Journal of Immunoassay and Immunochemistry, 31:103-110, 2010.
Mogi, et al., "Down-Regulation of NF-kB Led to Up-Regulation of NGF Production in Mouse Osteoblasts", Journal of Immunoassay and Immunochemistry, 31:92-101, 2010.
Mann, et al., "Endocytosis and targeting of exogenous HIV-1 Tag protein", The EMBO Journal, vol. 10, No. 7, pp. 1733-1739, 1991.
Fawell, et al., "Tat-mediated delivery of heterologous proteins into cells", Proc. Natl. Acad Sci, USA, vol. 91, pp. 664-668, Jan. 1994.
Wadia, et al., "Transducible TAT-HA fusogenic peptide enhances escape of TAT-fusion proteins after lipid raft macropinocytosis", Nature Medicine, vol. 10, No. 3, Mar. 2004.
Daftarian, et al., "Rejection of large HPV-16 expressing tumors in aged mice by a single immunization of VacciMax(R) encapsulated CTL/T helper peptides", Journal of Translational Medicine, 5:26, Jun. 7, 2007.

(Continued)

*Primary Examiner* — Julie Ha
(74) *Attorney, Agent, or Firm* — Duane Morris LLP; Gregory M. Lefkowitz; Jason M. Nolan

(57) ABSTRACT

The present disclosure is directed to providing: a new cell-penetrating peptide; and a composition for delivering a biologically active substance, a composition for gene therapy, a method for delivering a biologically active substance and a method for gene therapy using the same. The cell-penetrating peptide of the present disclosure can effectively deliver a protein into human cells and tissues, can deliver a protein with higher efficiency in comparison with a TAT peptide that is commercially used as a cell-penetrating peptide, and can also be usefully used in delivering a biologically active substance such as a protein, a genetic material, a chemical compound, etc. which may be used for a therapeutic purpose into cells.

18 Claims, 12 Drawing Sheets

(56) References Cited

OTHER PUBLICATIONS

Sutmuller, et al., "Adoptive T Cell Immunotherapy of Human Uveal Melanoma Targeting gp1001", The American Association of Immunologists, 2000.

Ota, et al., "Cellular Processing of a Multibranched Lysine Core with Tumor Antigen Peptides and Presentation of Peptide Epitopes Recognized by Cytotoxic T Lymphocytes on Antigen-presenting Cells", Cancer Research, 62, Mar. 1, 2002.

Kawamura, et al., "In Vivo Geneation of Cytotoxic T Cells from Epitopes Displayed on Peptide-Based Delivery Vehicles", The American Association of Immunologists, 2002.

\* cited by examiner

CELL PENETRATING PEPTIDE AND METHOD FOR DELIVERING BIOLOGICALLY ACTIVE SUBSTANCE USING SAME

CROSS-REFERENCE TO RELATED APPLICATIONS

This application is a § 371 national stage entry of International Application No. PCT/KR2015/002305, filed on Mar. 10, 2015, which claims priority to South Korean Patent Application No. 10-2014-0027918, filed on Mar. 10, 2014, the entire contents of which are incorporated herein by reference.

SEQUENCE LISTING

The instant application contains a Sequence Listing which has been submitted electronically in ASCII format and is hereby incorporated by reference in its entirety. Said ASCII copy, created on Oct. 27, 2016, is named G1035-09201_SL.txt and is 4,453 bytes in size.

TECHNICAL FIELD

The present disclosure relates to a system which delivers a biologically active substance that plays a role in cells into cells.

BACKGROUND ART

In general, biologically active polymeric substances such as proteins and DNAs cannot enter cells through cell membranes because they cannot pass through phospholipid bilayers. However, cell-penetrating peptides are known which can cross the cell membrane without the help of receptors or other molecules.

The cell-penetrating peptides, also called PTDs (protein transduction domains) or MTS (membrane-translocating sequences), can be associated or mixed with cargo such as proteins, DNAs, RNAs, etc. and deliver the cargo into cells through the cell membrane and also into the cytoplasm, cell organelles and nuclei (Endoh and Ohtsuki, 2010; Joliot and Prochiantz, 2004; Mogi and Kondo, 2010).

Tat is the first protein that has been found to penetrate the cell membrane during HIV-1 (human immunodeficiency virus-1) infection. The TAT peptide (YGRKKRRQRRR (SEQ ID NO: 15)) derived therefrom is the most frequently used and actively studied (Mann, D. A. et al., *EMBO J* 10: 1733-1739, 1991).

β-galactosidase, horseradish peroxidase, RNase A, the translocation domain of *Pseudomonas* exotoxin A (PE), etc. have been delivered into cells using the TAT peptide for researches of their functions and intracellular localization (Fawell, S. et al., *PNAS* 91: 664-668, 1994). It has been found that the TAT peptide enters the cells by interacting with heparan sulfate on the cell membrane, followed by endocytosis wherein lipid rafts are involved (Jehangir S. W. et al., *Nature Med* 10: 310-315, 2004).

In addition, penetratin (Antp), consisting of 16 amino acids, which is derived from Antennapedia homeoprotein and an essential transcription factor in the development of a fruit fly, cell-penetrating peptide VP22 which is derived from the VP22 protein expressed by HSV-1 (herpes simplex virus type 1), transportan, consisting of 27 amino acids, which has been artificially synthesized, polyarginine which has been obtained by artificially repeating the arginine residues expected to play the most important role in cell-penetrating peptides, etc. are well known as cell-penetrating peptides.

These existing cell-penetrating peptides may cause side effects such as immune responses when used in human bodies because they are derived from the proteins of viruses such as HIV-1, derived from the proteins expressed by other species such as fruit fly or artificially synthesized based on the amino acid sequence analysis of the previously known cell-penetrating peptides.

In addition, they are more likely to cause unwanted immune responses because they consist of relatively long amino acid chains. And, the efficiency of linking with biologically active substances to be delivered into cells is often low because they may affect the structure and function of the proteins to be delivered.

DISCLOSURE

Technical Problem

The present disclosure is directed to providing a cell-penetrating peptide, which is less likely to cause immune responses than existing cell-penetrating peptides and exhibits excellent effect of delivering a biologically active substance, and a composition for delivering a biologically active substance, a composition for gene therapy, a method for delivering a biologically active substance and a method for gene therapy using the same.

Technical Solution

The present disclosure provides a cell-penetrating peptide having a sequence of $(X1)_n$-X2-(cysteine)-$(X3)_m$. n is an integer from 3 to 14, m is an integer from 4 to 14, each of X1 and X3 is independently arginine, lysine or histidine and X2 is alanine, glycine, proline, tryptophan, phenylalanine, leucine, isoleucine, methionine, valine, arginine, lysine or histidine.

The present disclosure also provides a fusion product in which the cell-penetrating peptide is fused with a biologically active substance.

The present disclosure also provides a composition for delivering a biologically active substance into cells or tissues, which contains the fusion product as an active ingredient.

The present disclosure also provides a composition for gene therapy, which contains a fusion product of the cell-penetrating peptide with a genetic material as an active ingredient.

The present disclosure also provides a recombinant expression vector which expresses a recombinant protein in which the cell-penetrating peptide is fused with a biologically active protein.

The present disclosure also provides a recombinant expression vector which contains a DNA encoding the cell-penetrating peptide and a DNA encoding a biologically active protein.

The present disclosure also provides a method for delivering a biologically active substance, which includes: a step of preparing a delivery complex by binding the cell-penetrating peptide to a biologically active substance; and a step of injecting the prepared delivery complex into the body or cells of a non-human mammal.

The present disclosure also provides a method for gene therapy, which includes: a step of preparing a delivery complex by binding the cell-penetrating peptide to a genetic material; and a step of injecting the prepared delivery complex into the body or cells of a non-human mammal.

Advantageous Effects

A cell-penetrating peptide of the present disclosure can effectively deliver a protein into human cells and tissues, can deliver a protein with higher efficiency in comparison with a TAT peptide that is commercially used as a cell-penetrating peptide, and can also be usefully used in delivering a biologically active substance such as a protein, a genetic material, a chemical compound, etc. which may be used for a therapeutic purpose into cells.

BEST MODE

Figure 1:
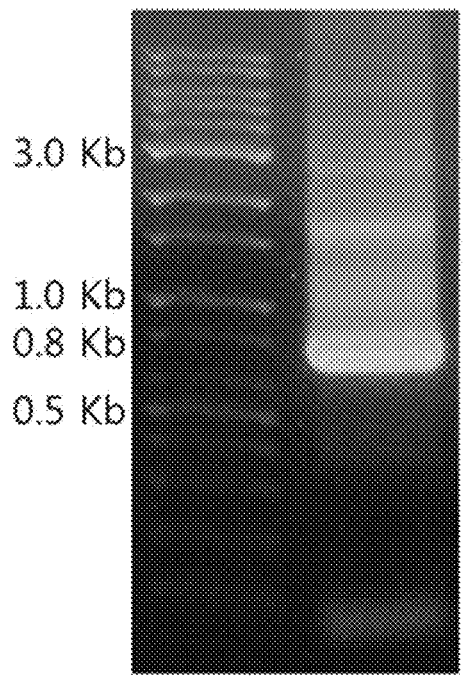
FIG. 1 shows a result of 1% agarose gel electrophoresis of a 789-bp double-stranded DNA fragment encoding AP-EGFP wherein AP is linked with EGFP of Preparation Example 2.

The present disclosure provides a cell-penetrating peptide having a sequence of $(X1)_n$-X2-(cysteine)-$(X3)_m$.

n is an integer from 3 to 14, specifically an integer from 3 to 6, and m is an integer from 4 to 14, specifically an integer from 4 to 7.

The cell-penetrating peptide consists of specifically 9-14, more specifically 9-12, most specifically 9-10, amino acids. When the number of the amino acids is smaller than the lower limit, the cell-penetrating effect decreases rapidly. And, when it exceeds the upper limit, the likelihood of immune response increases.

In the cell-penetrating peptide, each of X1 and X3 is independently a positively charged amino acid, arginine (Arg, R), lysine (Lys, K) or histidine (His, H), specifically arginine or lysine. $(X1)_n$ is formed by n positively charged amino acids X1. The n amino acids may be the same or different positively charged amino acids. Similarly, $(X3)_m$ is formed by m positively charged amino acids which may be different from each other.

In the cell-penetrating peptide, X2 is a nonpolar or positively charged amino acid, alanine (Ala, A), glycine (Gly, G), proline (Pro, P), tryptophan (Trp, W), phenylalanine (Phe, F), leucine (Leu, L), isoleucine (Ile, I), methionine (Met, M), valine (Val, V), arginine (Arg, R), lysine (Lys, K) or histidine (His, H), specifically alanine, tryptophan or arginine.

Specifically, the cell-penetrating peptide may be formed of an amino acid sequence of SEQ ID NO 1, SEQ ID NO 5, SEQ ID NO 8 or SEQ ID NO 12.

The present disclosure also provides a fusion product in which the cell-penetrating peptide is fused with a biologically active substance.

The biological activity means the activity of a substance delivered into the body or cells or an organism, related with physiological phenomena or therapeutic purposes. The biologically active substance may be a protein, a genetic material, a fat, a carbohydrate or a chemical compound. The genetic material may be a DNA or an RNA, and the chemical compound may be an anticancer drug, a therapeutic agent for an immune disease, an antiviral agent, an antibiotic or a growth, development or differentiation factor.

Because the cell-penetrating peptide is a very small peptide, it can minimize the possible biological interference with the biologically active substance. The fusion product of the cell-penetrating peptide and the biologically active substance may be delivered into the body by injecting via an intravenous, intraperitoneal, intramuscular, subcutaneous, intradermal, nasal, mucosal, inhalatory or oral route.

When the fusion product is desired to be delivered into specific cells, tissues or organs, the fusion product may be formed by binding the biologically active substance to an extracellular protein segment of a ligand that can selectively bind to a receptor specifically expressed in a specific cell, tissue organ or a monoclonal antibody (mAb) or a variant thereof that can selectively bind to the receptor or the ligand. The binding between the cell-penetrating peptide and the biologically active substance may be achieved in a nucleotide level by indirect linking by a cloning technique using an expression vector or by direct linking by chemical or physical covalent or noncovalent bonding between the peptide and the biologically active substance.

The present disclosure also provides a composition for delivering a biologically active substance into cells and a composition for gene therapy, which contain the fusion product as an active ingredient.

The composition allows a biologically active substance which cannot easily pass through a cell membrane to pass through it and directly act on a cell. Accordingly, the composition may provide a groundbreaking opportunity in the development of a drug delivery system.

The composition contains 0.0001-50 wt % of the fusion product based on the total weight of the composition.

The composition may contain, in addition to the fusion product, one or more active ingredient which exhibits the same or similar function.

The composition may be prepared by further containing, in addition to the active ingredient, one or more pharmaceutically acceptable carrier for administration. The pharmaceutically acceptable carrier may be one or more of saline, sterile water, Ringer's solution, a buffered saline, a dextrose solution, a maltodextrin solution, glycerol, ethanol and a liposome, and other commonly used additive such as an antioxidant, a buffer, a bacteriostat, etc. may be added if necessary. Also, it may be formulated as an injectable formulation such as an aqueous solution, a suspension, an emulsion, etc., a pill, a capsule, a granule or a tablet by additionally adding a diluent, a dispersant, a surfactant, a binder or a lubricant. And a target organ-specific antibody or ligand may be bound to the carrier for specific action on a target organ. In addition, the composition may be formulated according to particular diseases or ingredients by the method described in Remington's Pharmaceutical Sciences (latest edition), Mack Publishing Company, Easton Pa.

The composition may be delivered into the body by injecting via an intravenous, intraperitoneal, intramuscular, subcutaneous, intradermal, nasal, mucosal, inhalatory or oral route. The administration dosage may vary depending on the body weight, age, sex and diet of a subject, administration time, administration method, excretion rate, severity of a disease, etc. A daily dosage may be about 0.01-100 mg/kg, specifically 0.5-10 mg/kg, and may be administered once or several times a day.

The present disclosure also provides a recombinant expression vector which expresses a recombinant protein in which the cell-penetrating peptide is fused with a biologically active protein and a recombinant expression vector which contains a DNA encoding the cell-penetrating peptide and a DNA encoding a biologically active protein.

The biologically active protein may be delivered into cells or body and may exhibit an activity related with physiological phenomena or therapeutic purposes.

The recombinant expression vector may contain the sequences of the cell-penetrating peptide and the biologically active protein and a tag sequence facilitating the purification of the fused protein, e.g., a continuous histidine codon, a maltose-binding protein codon, a Myc codon, etc. and may further contain, e.g., a fusion partner for increasing the solubility of the fusion product. For stabilization of the entire structure and function of the recombinant protein or flexibility of the protein encoded by each gene, it may further contain a spacer amino acid or base sequence. Examples of the spacer include, but are not limited to, AAY (P. M. Daftarian et al., *J Trans Med* 2007, 5:26), AAA, NKRK (SEQ ID NO: 17) (R. P. M. Sutmuller et al., *J Immunol.* 2000, 165: 7308-7315) or one or several lysine residues (S. Ota et al., *Can Res.* 62, 1471-1476; K. S. Kawamura et al., *J Immunol.* 2002, 168: 5709-5715). Also, a marker or reporter gene sequence for identifying the delivery of a sequence specifically cleaved by an enzyme in order to remove undesired portion from the recombinant protein or an expression-regulating sequence into cells may be contained, although not being limited thereto.

The expression-regulating sequence used in the recombinant expression vector may be a regulatory domain including a promoter which is specific for cells, tissues or organs to which or in which the target DNA and/or RNA is selectively delivered or expressed.

The present disclosure also provides a method for delivering a biologically active substance, which includes: a step of preparing a delivery complex by binding the cell-penetrating peptide to a biologically active substance; and a step of injecting the prepared delivery complex into the body or cells.

The binding between the cell-penetrating peptide and the biologically active substance may be achieved in a nucleotide level by indirect linking by a cloning technique using an expression vector or by direct linking by chemical or physical covalent or noncovalent bonding between the peptide and the biologically active substance. The delivery complex of the peptide and the biologically active substance may be injected into the body or cells via an intravenous, intraperitoneal, intramuscular, subcutaneous, intradermal, nasal, mucosal, inhalatory or oral route. The delivery method may be applied not only to delivery to cultured cells but also to general in-vivo delivery, i.e., delivery to animal cells, animal tissues or animal bodies.

The present disclosure also provides a method for gene therapy, which includes: a step of preparing a delivery complex by binding the cell-penetrating peptide to a genetic material; and a step of injecting the prepared delivery complex into the body or cells of a non-human mammal.

The cell-penetrating peptide and the genetic material may be bound by direct linking by chemical or physical covalent or noncovalent bonding. The delivery complex of the genetic material may be injected into the body or cells via the same route as described above. The therapeutic method may be applied not only to delivery to cultured cells but also to general in-vivo delivery, i.e., delivery to animal cells, animal tissues or animal bodies.

The delivery complex of the genetic material is nonimmunogenic and noninflammatory and is not limited by the size of a plasmid because DNA is not packaged in a vector organism such as a retrovirus or an adenovirus. Accordingly, it can be used in recombinant gene-expressing structures of any practical sizes.

Mode for Invention

Hereinafter, the present disclosure will be described in detail through specific examples. However, the following examples are for illustrative purposes only and it will be apparent to those of ordinary skill in the art that the scope of the present disclosure is not limited by the examples.

Preparation Example 1: Synthesis and Purification of Peptides

Peptides having amino acid sequences of SEQ ID NOS 1-12 were synthesized.

After synthesizing sense and antisense oligodeoxynucleotides corresponding to the amino acid sequences, followed by removal of secondary or tertiary structures (denaturation) at 95° C. for 3 minutes, double-stranded DNAs were prepared by changing temperature to 50° C. and then to 72° C. For insertion into a pRSET-b vector, restriction enzyme-specific sequences were inserted into 5' and 3' sites in addition to the sense and antisense oligodeoxynucleotides. Then, the sequences were amplified in large quantities by transforming into E. coli. After confirming the integrity of the sequences, expression was induced in E. coli.

In order to fuse the peptide having an amino acid sequence of SEQ ID NO 1 (hereinafter also referred to as 'AP') with an enhanced green fluorescent protein (EGFP), a primer was constructed which allows linking of EGFP at the N-terminal of AP. After producing an AP-EGFP gene through PCR, it was inserted into a vector (pRSET-b). The protein was expressed in E. coli and then purified to measure intracellular delivery effect.

Preparation Example 2: Preparation of Double-Stranded DNA Encoding AP Having EGFP Linked at N-Terminal A forward primer was constructed by adding a DNA base sequence which encodes the peptide having an amino acid sequence of SEQ ID NO 1 to a DNA base sequence which encodes part of the N-terminal of an enhanced green fluorescent protein (hereinafter also referred to as 'EGFP').

A forward primer of SEQ ID NO 13 contains a NheI restriction enzyme recognition site for DNA cloning at the 5' end and a BamHI restriction enzyme recognition site between the base sequences of AP and EGFP. Meanwhile, a reverse primer of SEQ ID NO 14 was constructed for amplification of AP-EGFP by PCR. The reverse primer contains a DNA base sequence which encodes part of the C-terminal of EGFP. For DNA cloning, a HindIII restriction enzyme recognition site was inserted at the 5' end of the primer.

PCR was conducted using the pRSETb vector containing the EGFP gene as a template and using the primers of SEQ ID NO 13 and SEQ ID NO 14. After initial thermal denaturation at 95° C. for 3 minutes, PCR was carried out using a PCR machine (Bio-Rad) for 30 cycles (thermal denaturation of the template at 95° C. for 20 seconds→polymerization between the primers and the template at 50° C. for 20 seconds→extension at 72° C. for 30 seconds).

The obtained amplification product of AP-EGFP was subjected to 1% agarose gel electrophoresis. It was confirmed that a 789-bp DNA fragment was amplified (FIG. 1).

Preparation Example 3: Preparation of pRSETb Vector in which AP-EGFP is Inserted In order to express the AP-EGFP protein, the 789-bp DNA fragment prepared in Preparation Example 2 was inserted into the protein expression vector pRSETb using a restriction enzyme and a ligase.

The DNA fragment amplified in Preparation Example 2 was treated with NheI and HindIII (NEB) enzymes to make the 5'/3' ends of the DNA sticky. Meanwhile, pRSETb was treated with the same restriction enzymes to prepare a linear pRSETb vector having NheI and HindIII insertion sites. After each enzymatic reaction, the product was separated using a PCR purification kit (Cosmo Genetech).

Figure 2:
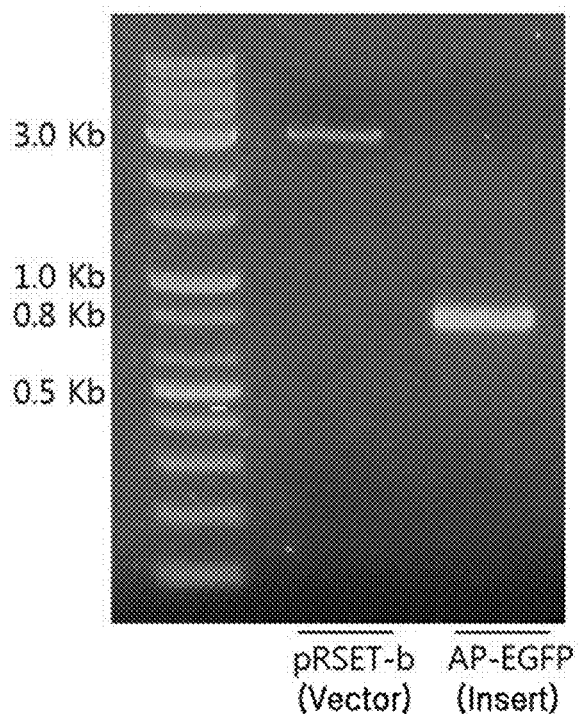
FIG. 2 shows a result of treating an AP-EGFP DNA fragment (789 bp) of Preparation Example 3 and a pRSET-b vector (2.9 Kb) with NheI and HindIII restriction enzymes for insertion of the AP-EGFP DNA fragment and quantifying the amount of DNA by 1% agarose gel electrophoresis.

The separated AP-EGFP double-stranded DNA fragment and pRSET-b vector were treated with T4 ligase (NEB) at 25° C. for 2 hours. The concentrations of the AP-EGFP double-stranded DNA fragment and pRSET-b vector were analyzed by 1% agarose gel electrophoresis (FIG. 2).

Figure 3:
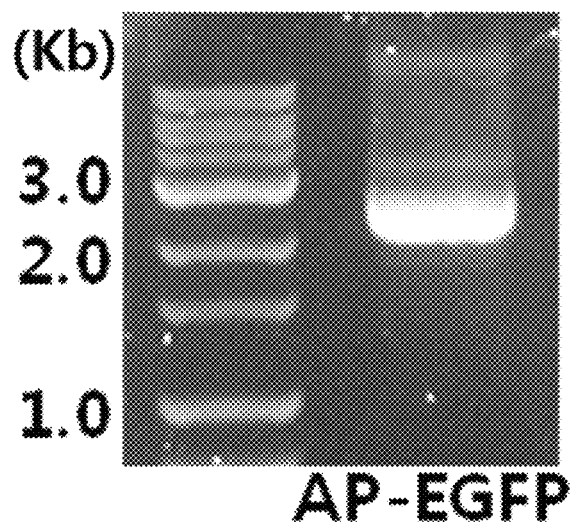
FIG. 3 shows a result of transforming DH5a *E. coli* with a pRSET-b vector in which a DNA fragment encoding AP-EGFP is inserted of Preparation Example 3, culturing a colony selected from culturing on a plate LB medium in a liquid LB medium, isolating DNA through plasmid mini preparation and conducting 1% agarose gel electrophoresis.

The resulting pRSETb vector in which AP-EGFP is inserted was transformed into DH5a E. coli and the transformed E. coli which formed a colony when cultured on a plate LB medium containing 50 µg/mL ampicillin as an antibiotic was selected. The selected E. coli colony was cultured again in a liquid LB medium containing 50 µg/mL ampicillin and then the plasmid vector was separated using a plasmid mini preparation kit (Cosmo Genetech) (FIG. 3).

Figure 4:
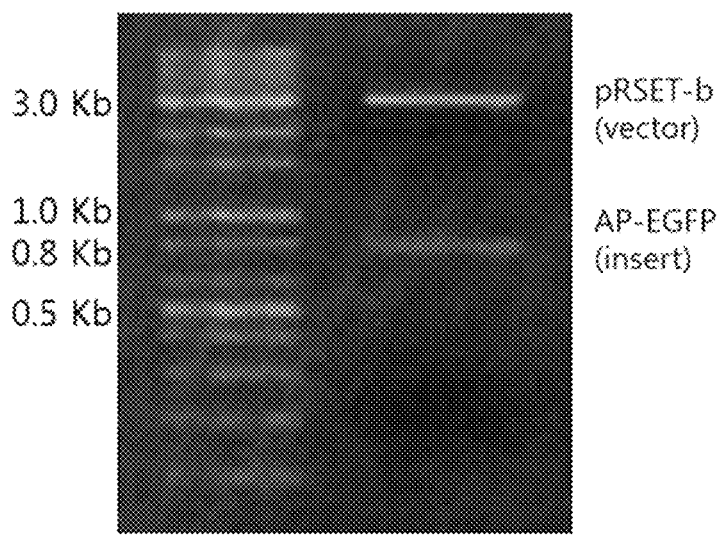
FIG. 4 shows a result of treating a confirming that a plasmid DNA isolated in Preparation Example 3 consists of a DNA fragment encoding AP-EGFP (789 bp) and a pRSET-b vector (2.9 Kb) by treating with NheI and HindIII restriction enzymes and conducting 1% agarose gel electrophoresis.
Figure 5:
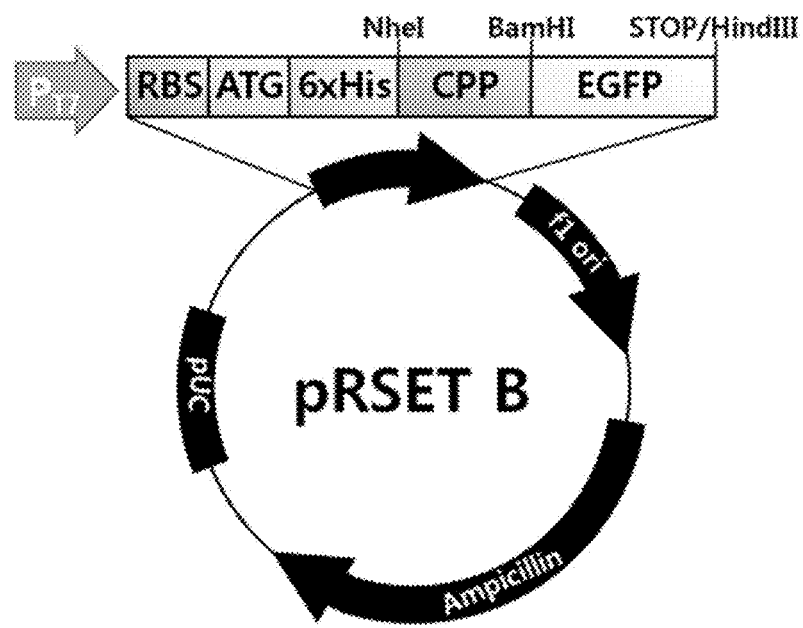
FIG. 5 is a schematic of a pRSET-b vector in which AP-EGFP is inserted of Preparation Example 3. Figure discloses "6xHis" as SEQ ID NO: 16.

In order to confirm that the separated plasmid vector is a pRSETb vector in which AP-EGFP is inserted, it was treated with NheI and HindIII restriction enzymes and then analyzed by 1% agarose gel electrophoresis. As a result, it was confirmed that the 789-bp AP-EGFP DNA fragment is inserted in the 2.9-kbp pRSET-b vector (FIG. 4). This could also be confirmed by DNA base sequence analysis (Bionics). The structure of the pRSETb vector in which AP-EGFP is inserted is shown in FIG. 5.

Preparation Example 4: Expression and Purification of AP-EGFP Protein in E. coli The pRSETb vector in which AP-EGFP is inserted of Preparation Example 3 was transformed into E. coli BL21 (DE3) star pLysS. A colony formed on a plate LB medium containing 34 µg/mL chloramphenicol and 50 µg/mL ampicillin as antibiotics was cultured in 50 mL of a liquid LB medium at 37° C. for 10 hours and then transferred to 500 mL of a fresh liquid LB medium. After culturing at the same temperature until the quantity of E. coli measured by a spectrophotometer reached O.D 0.5, IPTG (isopropyl β-D-1-thiogalactopyranoside) was added to a concentration of 1 mM, the E. coli was further cultured in a shaking incubator set to 20° C. and 150 rpm for 14 hours. The protein expressed by the E. coli contained a 6×-His tag SEQ ID NO: 16) upstream of AP-EGFP of the pRSET-b vector. The protein was purified as follows.

Figure 6:
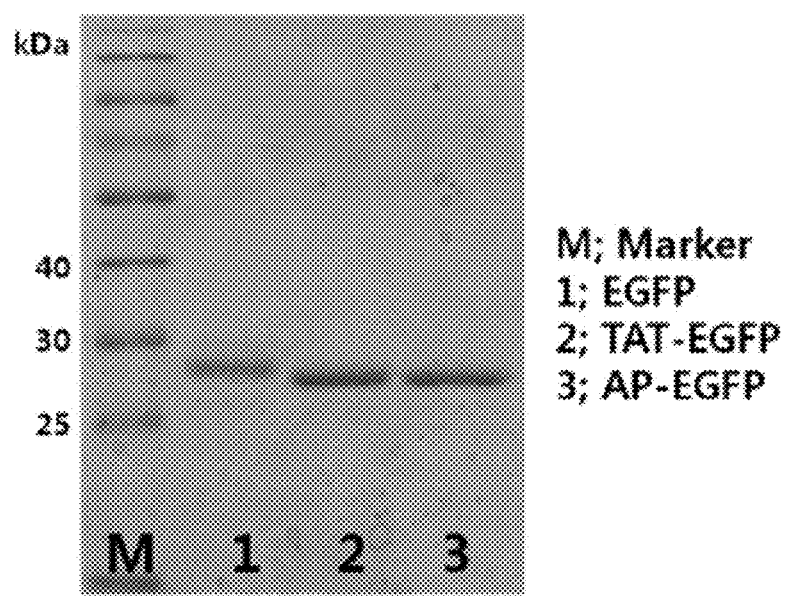
FIG. 6 shows a result of 12% SDS gel electrophoresis of a purified AP-EGFP protein of Preparation Example 4, an EGFP protein in which a cell-penetrating peptide is not linked as a negative control and a TAT-EGFP protein, which is the most widely known cell-penetrating peptide, as a positive control.

The culture was centrifuged and then suspended in a lysis buffer (0.5 M NaCl, 5 mM imidazole, 20 mM Tris-HCl, pH 8.0) under a native condition. The E. coli was allowed to be suspended in the lysis buffer for 10 minutes in order to disrupt the cell wall and cell membrane. Then, the cells were disrupted using the ultrasonic cell crusher VCX-130 (Sonics & Materials) and then centrifuged. The separated supernatant was filtered once through a 0.45-µm filter (Advantec) and was allowed to bind to Ni-NTA agarose (Qiagen) at room temperature for 1 hour. Then, only the protein product binding to the Ni-NTA agarose was made to bind to a histidine column (His-column, Bio-Rad). After washing with a 20 mM imidazole solution, the protein was eluted using a 250 mM imidazole solution. Finally, AP-EGFP was purified from the eluted protein product using a PD-10 desalination column (Amersham Biosciences) (FIG. 6).

Test Example 1: Comparison of Delivery Efficiency of AP-EGFP Protein into Jurkat Cells which are Immortalized Human T Cells The AP-EGFP protein purified in Preparation Example 4 was delivered into Jurkat cells which are immortalized human T cells and the efficiency was investigated. Jurkat cells were cultured using an RPMI medium (HyClone) and then transferred to a 24-well plate (SPL Life Sciences) containing 350 µL of an RPMI medium, with $1\times10^6$ cells per well in 100 µL of an RPMI medium. Then, after mixing the protein with 50 µL of D-PBS (Welgene) to a total volume of 500 µL, the cells were treated with the protein under various conditions as follows. Unless specified otherwise hereinafter, the cells were treated with each protein at 5 µM and then cultured in a 5% $CO_2$ incubator at 37° C. for 1 hour.

First, after treating with the AP-EGFP protein at a concentration of 1 µM, the cells were cultured in a 5% $CO_2$ incubator at 37° C. for 1 hour. As controls, the EGFP protein not containing AP and the TAT-EGFP protein as an existing cell-penetrating peptide were used. After 1 hour, all the cells were recovered and transferred to a tube. After performing centrifugation, the supernatant was removed. A procedure of washing the cells with 1 mL of D-PBS, resuspending and then centrifuging was repeated 2 times. After the washing, the obtained cells were resuspended finally in 500 µL of D-PBS and delivery efficiency of the protein into the cells was measured by measuring intracellular fluorescence by flow cytometry using a FACS machine (FACSCanto II, BD Science). As a result, it was confirmed that the AP-EGFP protein was delivered into the Jurkat cells in a concentration-dependent manner.

Figure 7:
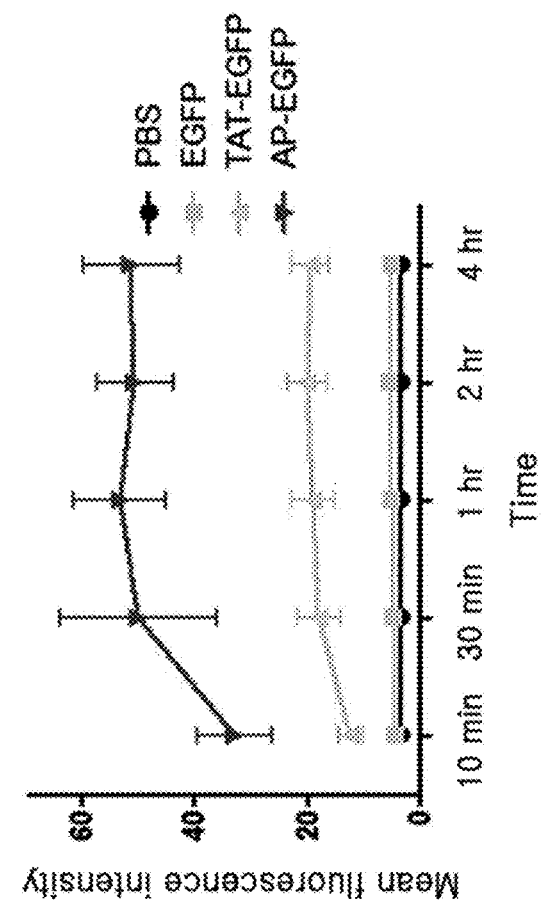
FIG. 7 shows a result of fluorescence intensity analysis by flow cytometry in Test Example 1 showing that an AP-EGFP protein is delivered into Jurkat cells in a concentration-dependent, time-dependent manner.
Figure 7:
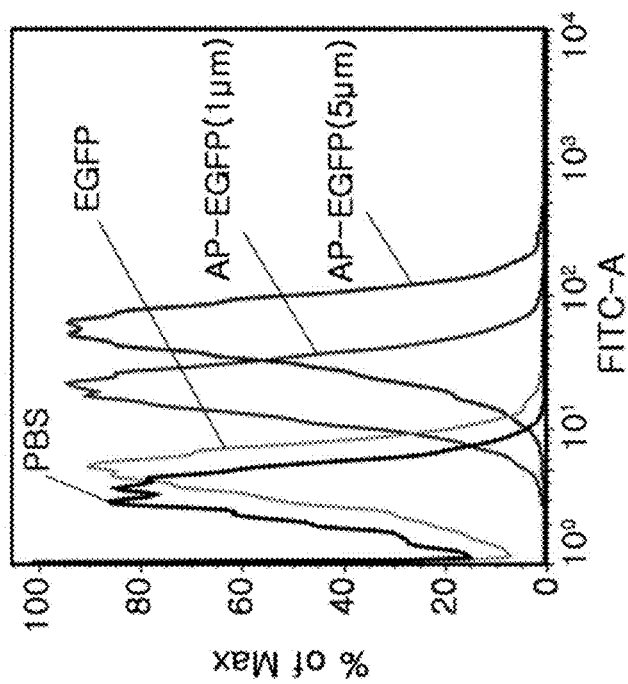

Then, after treating with the AP-EGFP protein at a concentration of 5 µM, the cells were cultured in a 5% $CO_2$ incubator at 37° C. for 30 minutes to 4 hours. After washing the cells as described above, intracellular fluorescence was measured by flow cytometry. As a result, it was confirmed that the AP-EGFP protein was delivered into the Jurkat cells in a concentration-dependent manner (FIG. 7).

Test Example 2: Comparison of Delivery Efficiency with Previously Known Cell-Penetrating Peptides For comparison of delivery efficiency with previously known cell-penetrating peptides, each protein was delivered into Jurkat cells in the same manner as described in Test Example 1 at the same concentration and for the same time.

Figure 8:
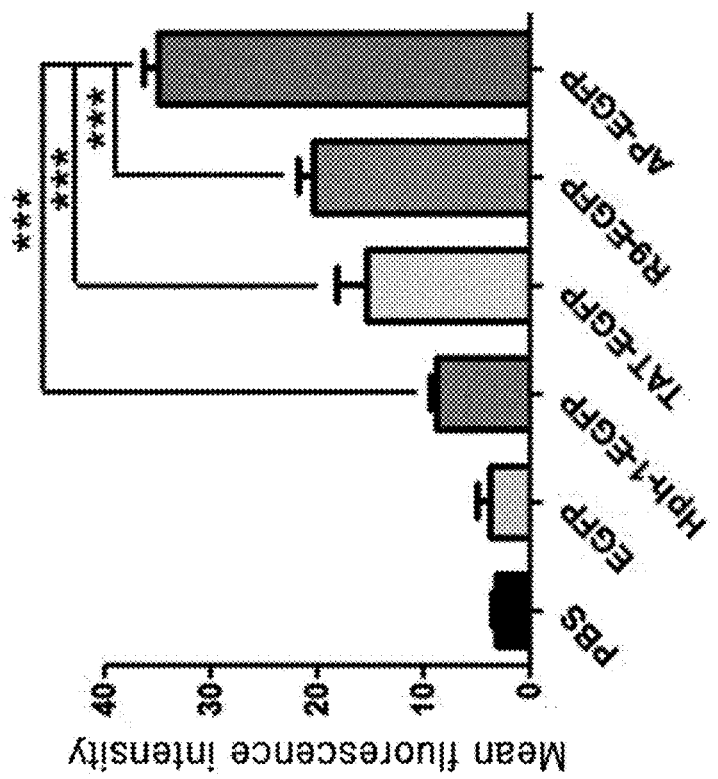
FIG. 8 shows a result of fluorescence intensity analysis by flow cytometry in Test Example 2 comparing the efficiency of delivery of AP into Jurkat cells with that of an existing cell-penetrating peptide as a positive control.
Figure 8:
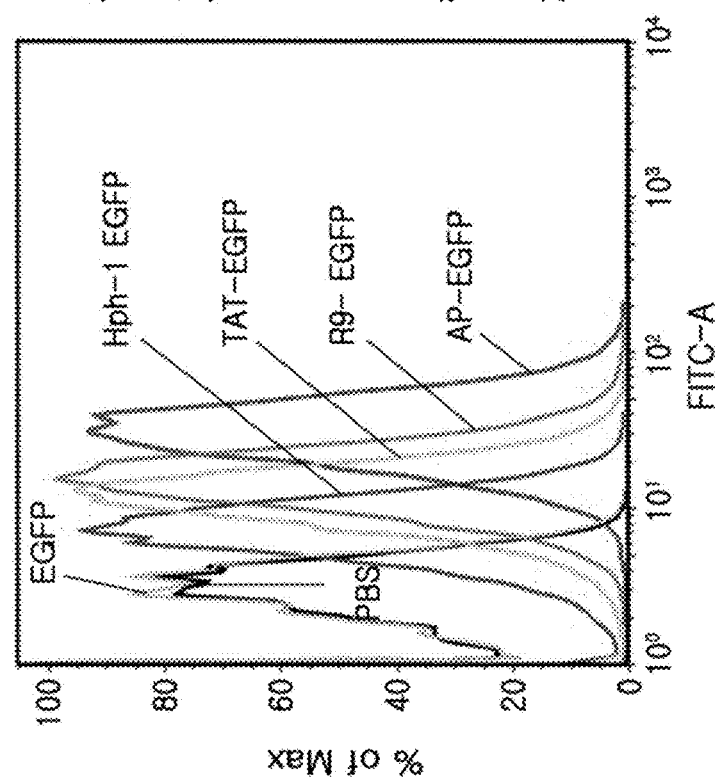

The EGFP protein not linked with a cell-penetrating peptide was used as a negative control and TAT-EGFP, R9-EGFP and Hph-1 EGFP in which EGFP (enhanced green fluorescent protein) is linked with each cell-penetrating peptide were used as positive controls. As a result, it was confirmed that the AP sequence discovered/developed in the present disclosure delivers the protein into Jurkat cells with higher efficiency than TAT (FIG. 8).

Text Example 3: Comparison of Protein Delivery Efficiency Depending on Substitution, Removal or Addition of Amino Acid In order to investigate the role of each amino acid constituting AP, various variants were prepared and analyzed for comparison.

(1) Comparison of Protein Delivery Efficiency Depending on Removal of Terminal Amino Acid First, variants with one arginine removed from the N-terminal of AP (AP_D1, SEQ ID NO 2), with one arginine removed from the C-terminal (AP_D2, SEQ ID NO 3) and with one arginine removed from each of the N- and C-terminals (AP_D3, SEQ ID NO 4) were prepared and they were compared with EGFP, AP-EGFP, TAT-EGFP and R9-EGFP as controls.

Figure 9:
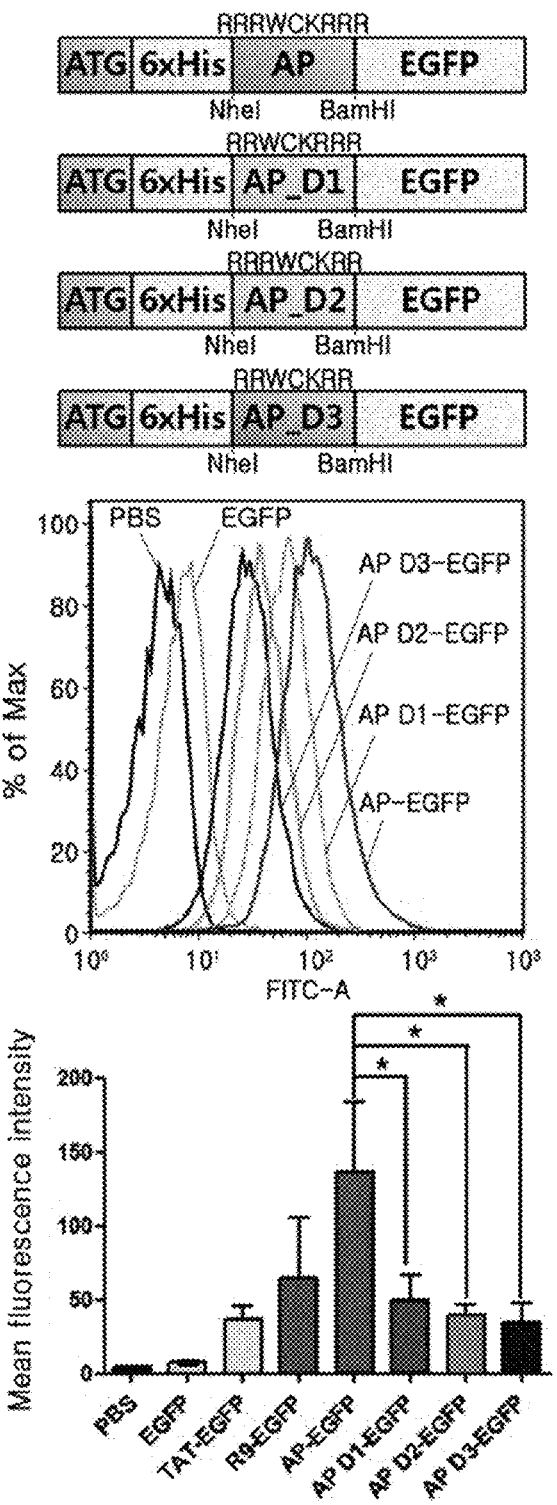
FIG. 9 shows a result of fluorescence intensity analysis by flow cytometry in Test Example 3 comparing the efficiency of delivery of arginine which occupies the largest portion of AP into cells with that of those having less arginine residues. Figure discloses SEQ ID NOS 1-4, respectively, in order of appearance and "6xHis" as SEQ ID NO: 16.

As a result, it was found out that, when one arginine is missing, i.e. when the number of X1 is smaller than 3 or when the number of X2 is smaller than 4, delivery efficiency decreases significantly as compared to AP. Accordingly, the critical meaning of the lower limit of the number of amino acids X1 and X2 in the delivery of the AP protein into cells was confirmed (FIG. 9).

(2) Comparison of Protein Delivery Efficiency Depending on Substitution of X2, Cysteine or X3

In order to investigate the role of tryptophan (X2), cysteine and lysine (first amino acid of X3), variants were prepared by substituting each amino acid with alanine or arginine. Alanine is suitable as a control because it has no charge, is the simplest and has a small size.

Figure 10:
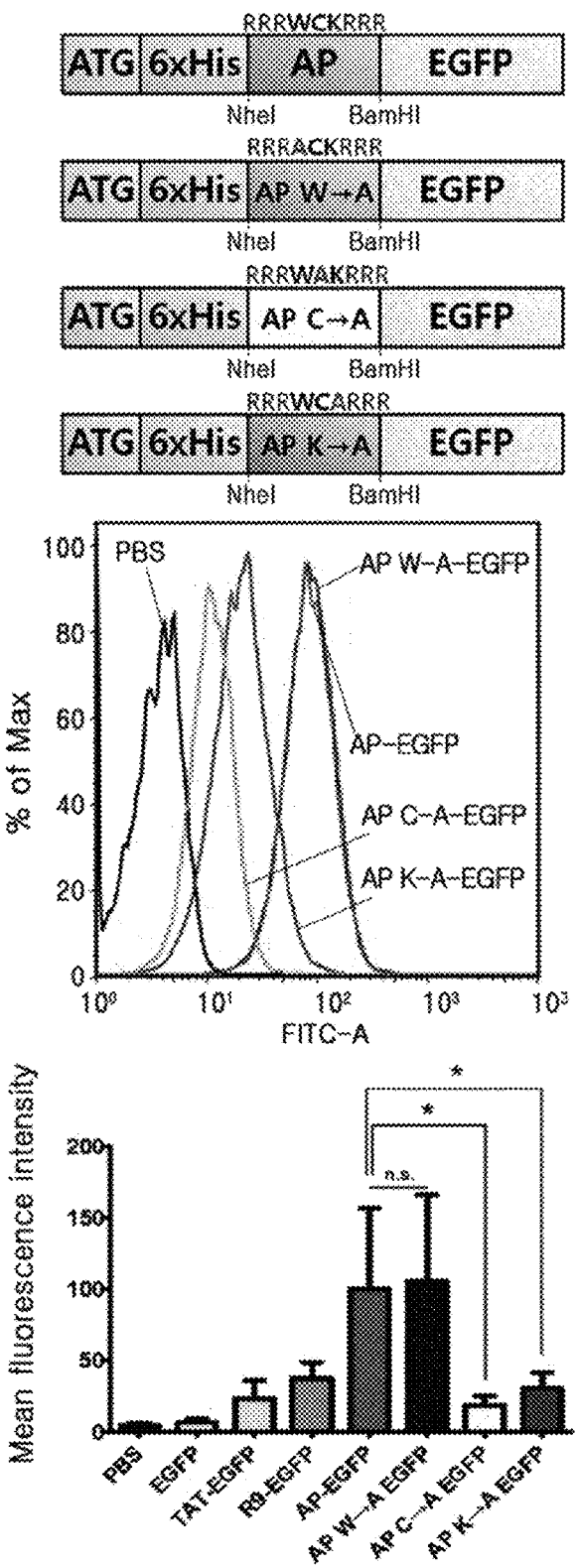
FIG. 10 shows a result of fluorescence intensity analysis by flow cytometry in Test Example 3 comparing the effect of tryptophan (X2), cysteine and lysine (first amino acid in X3) constituting AP on the delivery of AP into cells by replacing each of them with alanine. Figure discloses SEQ ID NOS 1 and 5-7, respectively, in order of appearance and "6xHis" as SEQ ID NO: 16.
Figure 11:
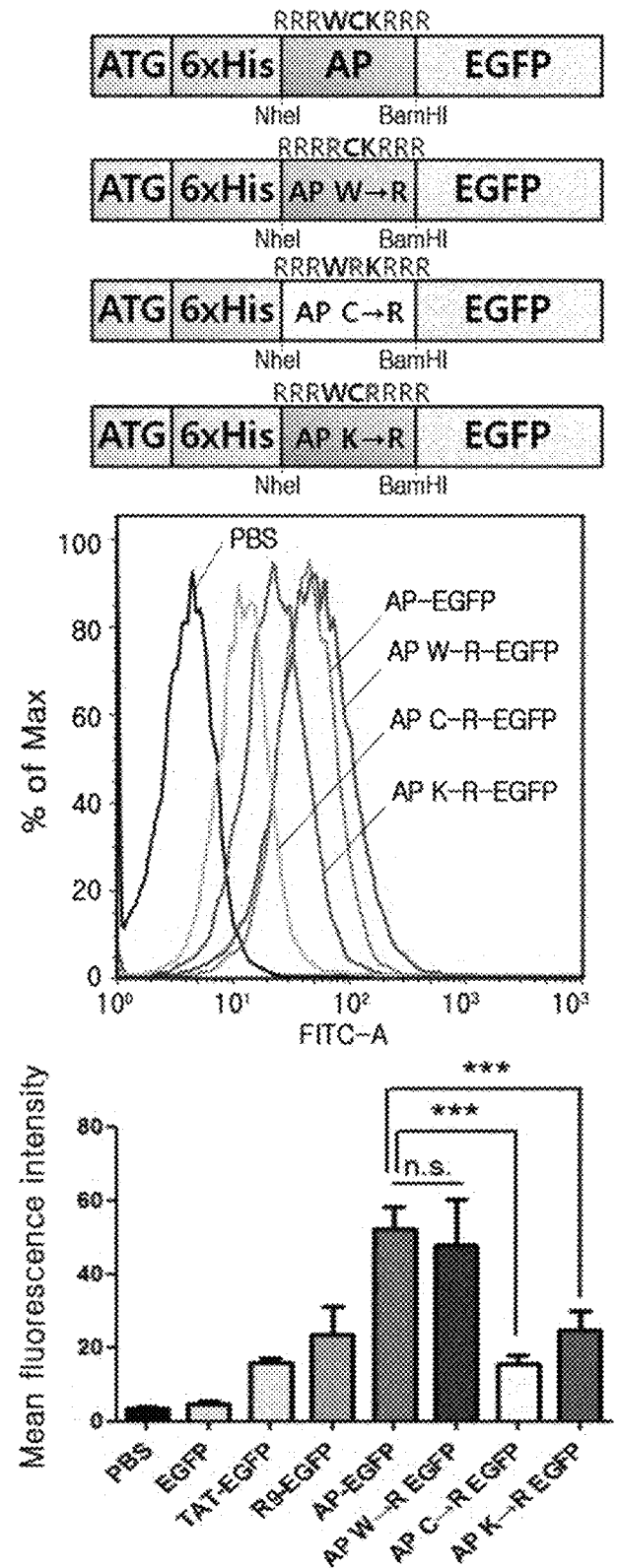
FIG. 11 shows a result of fluorescence intensity analysis by flow cytometry in Test Example 3 comparing the effect of tryptophan (X2), cysteine and lysine (first amino acid in X3) constituting AP on the delivery of AP into cells by replacing each of them with arginine. Figure discloses SEQ ID NOS 1 and 8-10, respectively, in order of appearance and "6xHis" as SEQ ID NO: 16.

A variant having a positively charged arginine was used as a control for comparison of efficiency with R9 which consists of 9 arginines (SEQ ID NO: 11). As a result, the alanine variant and the arginine variant showed similar patterns. Because no significant difference in efficiency was observed when tryptophan was replaced with other amino acid, it was confirmed not to contribute significantly to the functional role of AP. When arginine was substituted with other amino acid, the efficiency decreased greatly. It is though that the positively charged arginine plays a positive role. The greatest decrease in efficiency was observed when cysteine was substituted with other amino acid. This suggests that cysteine plays a very important functional role in AP (FIG. 10 and FIG. 11).

Text Example 4: AP's Cell-Penetrating Mechanism

In order to investigate whether AP is delivered into cells through endocytosis as the most widely known existing cell-penetrating peptide TAT, change in intracellular delivery depending on temperature was measured and it was investigated whether it is affected by other protein depending on the serum concentration of a medium. EGFP not linked with a cell-penetrating peptide was used as a negative control and TAT-EGFP was used as a positive control.

Figure 12:
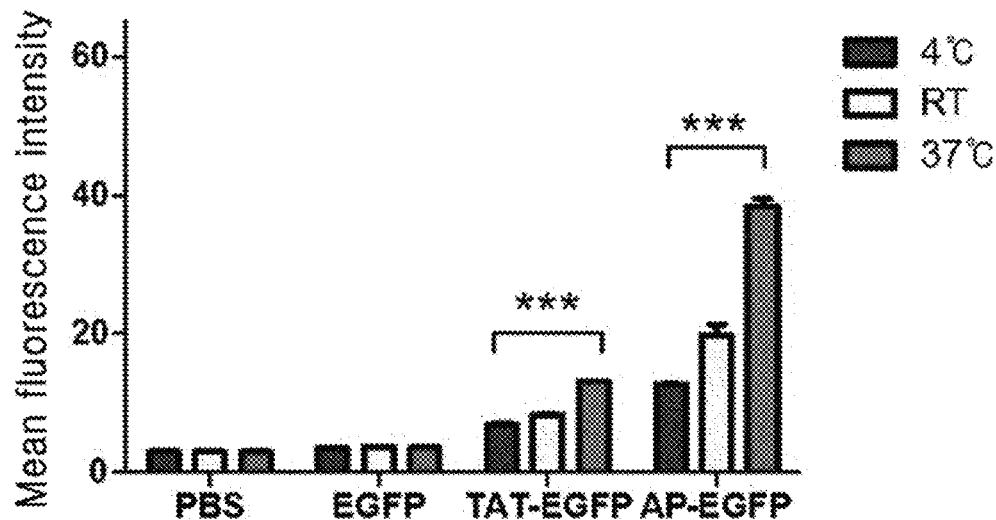
FIG. 12 shows a result of fluorescence intensity analysis by flow cytometry in Test Example 4 comparing the change in the delivery efficiency of AP into cells depending on change in temperature and serum concentration in a medium with that of existing cell-penetrating peptides as positive controls.
Figure 12:
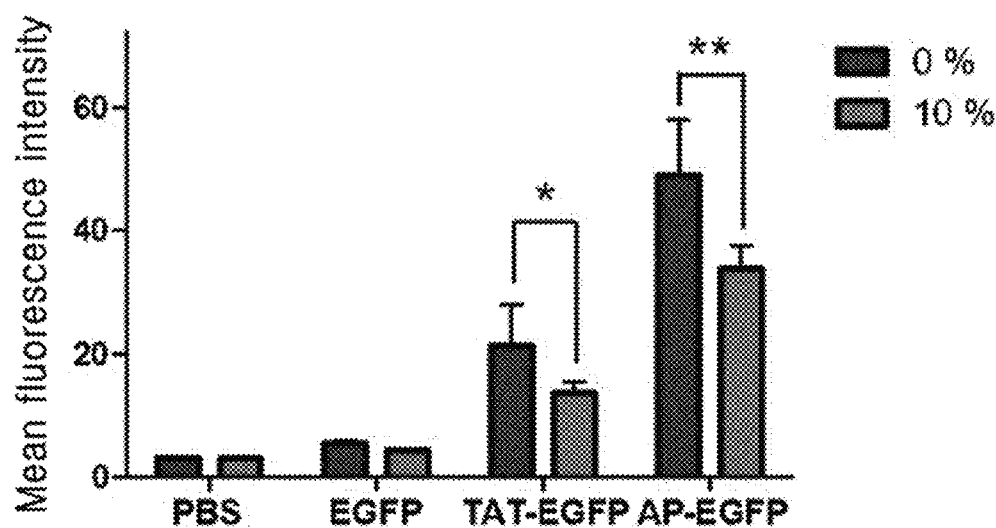

Jurkat cells were treated with each protein at 5 µM as described above at temperatures of 4° C., 25° C. and 37° C. independently for 1 hour. As a result, it was confirmed that the intracellular delivery was not affected by temperature unlike TAT. This suggests that AP is not delivered by energy-dependent endocytosis unlike TAT. In addition, it was confirmed that the delivery efficiency was higher than TAT at all temperatures (FIG. 12, top).

Also, the delivery efficiency of each protein (5 µM) was analyzed when the serum concentration in an RPMI medium was 0% and 10%, respectively. After treating with each protein, the cells were cultured at 37° C. for 1 hour. EGFP not linked with a cell-penetrating peptide was used as a negative control and TAT-EGFP was used as a positive control.

As a result, it was confirmed that the efficiency of the delivery of the AP-EGFP protein into cells through the cell membrane decreased with the serum concentration. This suggests that the cell-penetrating peptide is affected by competition or interaction with other proteins and confirms again the function of the AP according to the present disclosure as a cell-penetrating peptide. AP showed higher delivery efficiency than the positive controls at each serum concentration (FIG. 12, bottom).

Text Example 5: Intracellular Delivery Efficiency of AP-EGFP Depending on Heparin and MβCD Concentrations (1) Intracellular Delivery Efficiency of AP-EGFP Depending on Heparin Concentration With the expectation that treatment with heparin which can interfere with binding of the cell-penetrating peptide to heparan sulfate on cell surface would directly or indirectly affect the interaction, Jurkat cells were treated for 30 minutes with heparin (heparin sodium salt from porcine intestinal mucosa, Sigma) at different concentrations of 0 μm/mL, 10 μg/mL, 20 μg/mL and 50 μg/mL and then with 10 μM AP-EGFP whose final volume was made 100 μL with D-PBS. TAT-EGFP was used as a positive control for comparison. The cells were then cultured for 1 hour in a 5% $CO_2$ incubator at 37° C. 1 hour later, all the cells were recovered and transferred to a tube. After performing centrifugation, the supernatant was removed. A procedure of washing the cells with 1 mL of D-PBS, resuspending and then centrifuging was repeated 2 times. After the washing, the obtained cells were resuspended finally in 500 μL of D-PBS and delivery efficiency of the protein into the cells was measured by measuring intracellular fluorescence by flow cytometry using a FACS machine (FACSCanto, BD Science). As a result, it was confirmed that the AP-EGFP protein was delivered into the Jurkat cells in a concentration-dependent manner.

Figure 13:
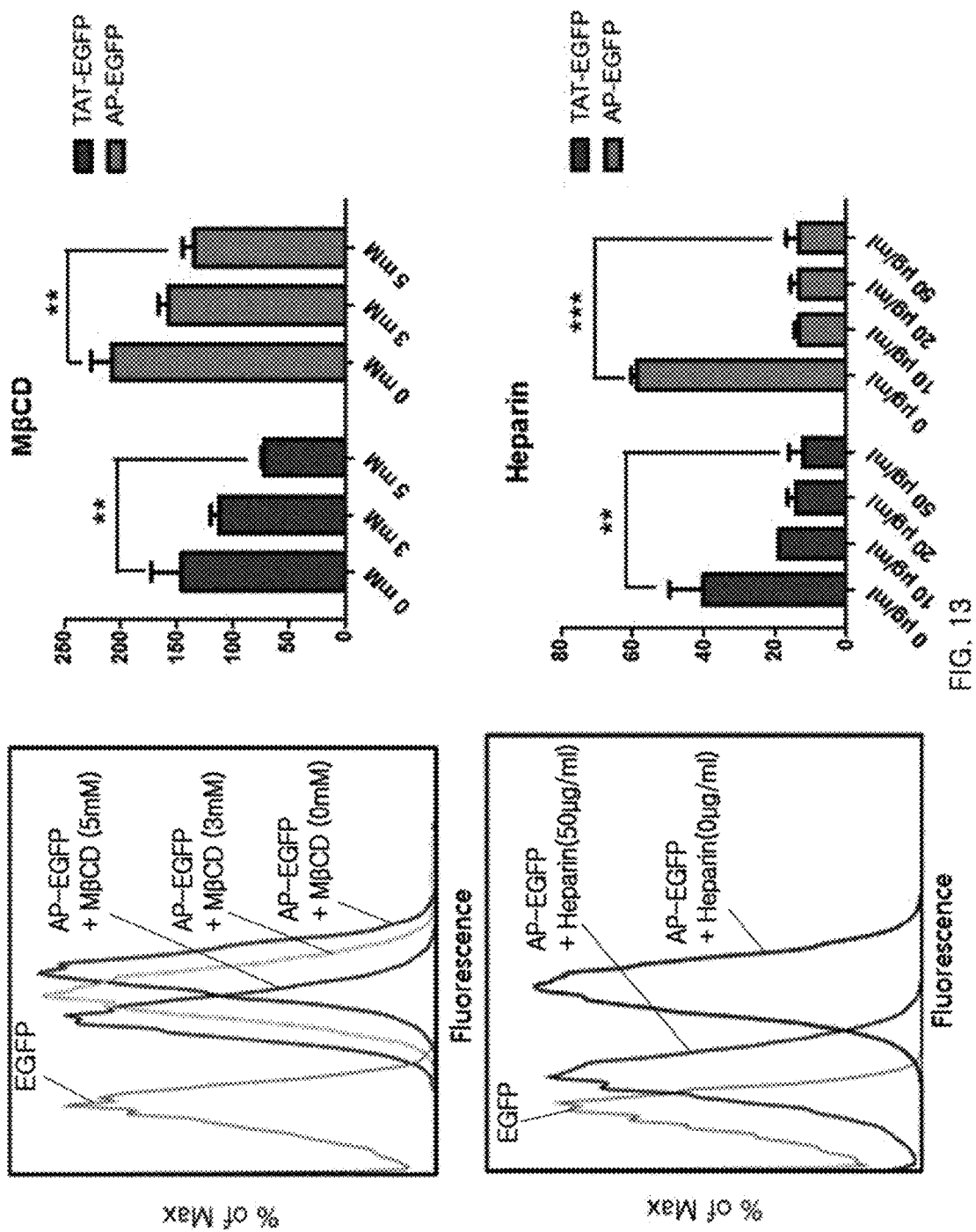
FIG. 13 shows a result of fluorescence intensity analysis by flow cytometry in Test Example 5 comparing the change in the delivery efficiency of AP-EGFP into cells depending on change in the concentration of heparin and MβCD (methyl-beta-cyclodextrin) with that of existing cell-penetrating peptides as positive controls.

As a result, it was confirmed that the intracellular delivery efficiency of AP-EGFP decreases remarkably with the heparin concentration (FIG. 13, top).

(2) Intracellular Delivery Efficiency of AP-EGFP Depending on MβCD Concentration Also, with the expectation that the intracellular delivery of AP-EGFP would be affected by endocytosis which is associated with the lipid raft constituting the phospholipid bilayer of the cell membrane, lipid-mediated endocytosis was inhibited in advance by treating with MβCD (methyl-beta-cyclodextrin) which is known to remove cholesterol from the cell membrane. After treating Jurkat cells with 0 mM, 3 mM or 5 mM MβCD for 20 minutes on ice, the cells were treated with 10 μM AP-EGFP for 1 hour. TAT-EGFP was used as a positive control for comparison. As a result, it was confirmed that the intracellular delivery efficiency of AP-EGFP decreases remarkably with the MβCD concentration (FIG. 13, bottom).

This also suggests that the cell-penetrating peptide is directly or indirectly affected by competition or interaction with other proteins and confirms again the function of the AP according to the present disclosure as a cell-penetrating peptide.

Text Example 6: Delivery of AP-EGFP into HeLa Cancer Cells

It was confirmed in Test Example 1 by flow cytometry that the AP protein is effectively delivered into cells. In order to investigate whether AP is actually delivered into cells together with the protein and where it exists in the cells, AP-EGFP was delivered into HeLa cells which are cervical cancer cells and analysis was conducted using a confocal microscope.

Figure 14:
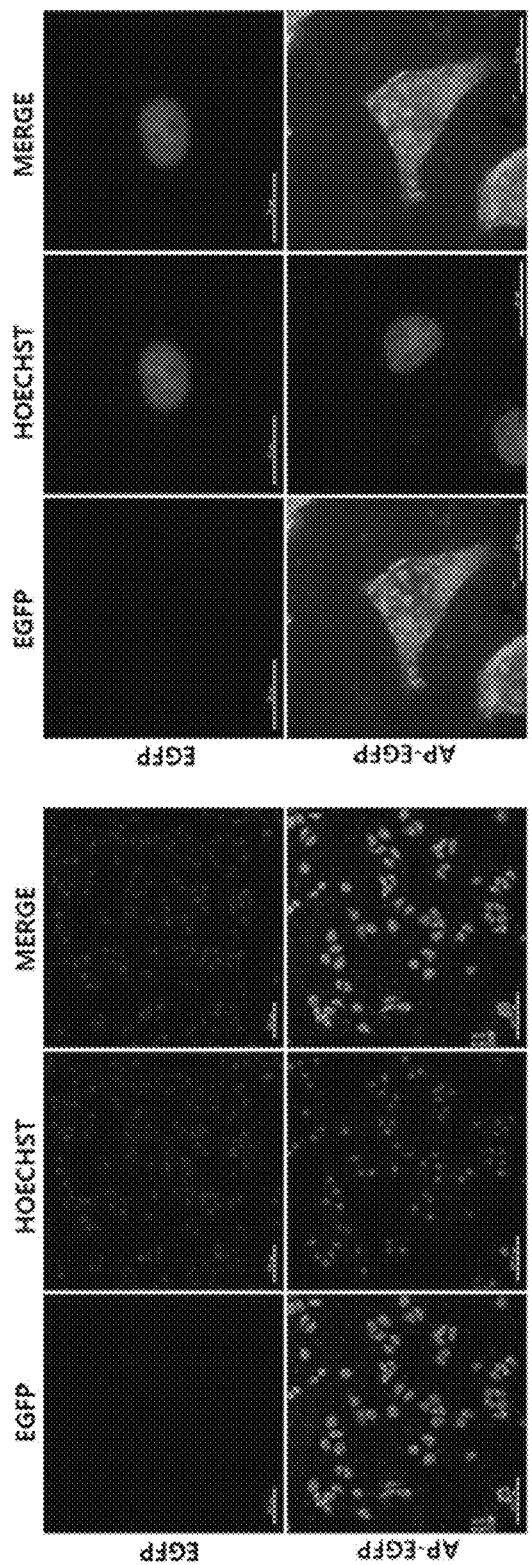
FIG. 14 shows fluorescence microscopic images showing that AP-EGFP is delivered into HeLa cells in Test Example 6.
Figure 14:
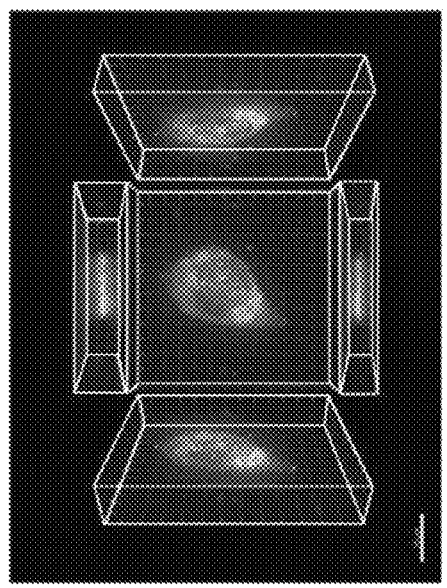

After seeding $1 \times 10^5$ HeLa cells on a circular cover glass (Marinfield) in each well of a 12-well plate (SPL Life Sciences), the cells were cultured for 18 hours in a DMEM medium (HyClone) so that the cells were attached to the cover glass. After completely discarding the medium by suction and adding 450 μL of fresh DMEM, the cells were treated with the AP-EGFP protein purified in Preparation Example (5 μM) whose final volume was made 50 μL by mixing with D-PBS. Then, the cells were incubated for 30 minutes in a 5% $CO_2$ incubator at 37° C. Then, after completely discarding the medium by suction to remove extracellular proteins, the cells were washed with 1 mL of D-PBS. This procedure was repeated 5 times. Then, the cells were fixed with 1 mL of formaldehyde (formaldehyde 37% solution, formalin, Sigma). After the fixation, the cells were washed 5 times with 1 mL of D-PBS. Then, the nuclei of the cells were stained with 500 μL of a Hoechst stain (Hoechst AG) diluted to 1:4000. After 10 minutes, the cells were washed 5 times with 1 mL of D-PBS. The prepared cover glass was mounted on a slide glass using a mounting medium (Sigma) and the location and intracellular delivery of the green fluorescent protein were observed using the fluorescence microscope AX-10 (Carl Zeiss). As a result, it was confirmed that the AP-linked green fluorescent protein is delivered into cells through the cell membrane and is present in the cytoplasm (FIG. 14).

Text Example 7: Delivery of AP-EGFP into Mouse Organs

Figure 15:
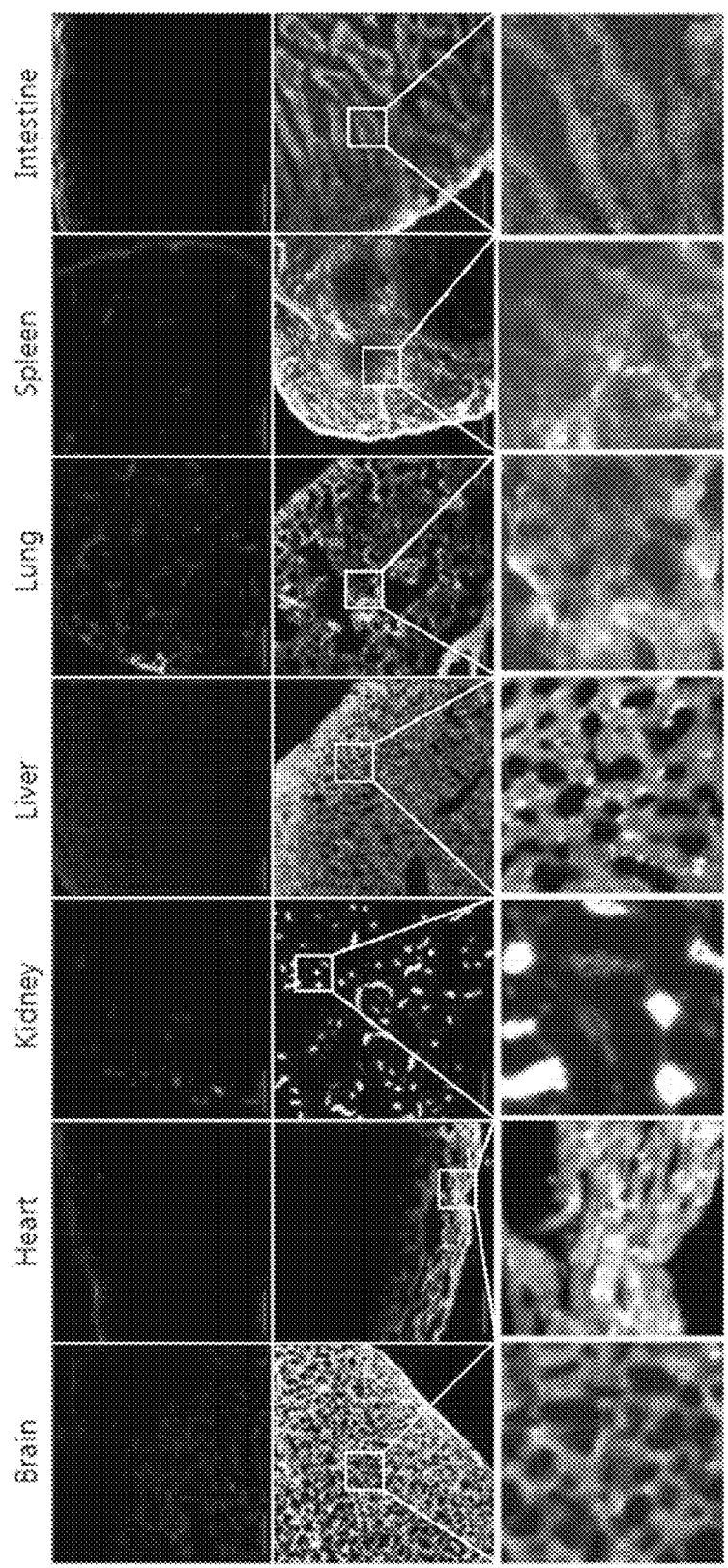
FIG. 15 shows fluorescence microscopic images showing that AP-EGFP is delivered into the cells of mouse organs in Test Example 7.

It was confirmed in Test Example 1 by flow cytometry that the AP protein is effectively delivered into cells and in Test Example 6 that AP-EGFP is delivered into HeLa cancer cells. In order to investigate whether AP is delivered under the actual in-vivo condition and, if so, how much can be delivered to which organs, 5 mg of the AP-EGFP protein was intraperitoneally injected to a 6-week-old female C57BL/6 mouse. 2 hours later, organs such as the brain, heart, kidney, liver, lung, spleen, intestine, etc. were taken and fixed with 4% paraformaldehyde. After washing 2-3 times with D-PBS, frozen blocks were prepared using the OCT compound. After preparing 6 μm-thick sections using a cryostat, the slide samples were observed under a fluorescence microscope in order to confirm the delivery of AP-EGFP into the organ cells. The slide samples were stained with Hoechst stain for 10 minutes and the intracellular delivery was investigated by overlapping with the fluorescent protein. EGFP not linked with a cell-penetrating peptide was used as a control. As a result, it was confirmed that the AP-linked green fluorescent protein was delivered better into the cells of the brain, heart, kidney, liver, lung, spleen, intestine, etc. than EGFP (FIG. 15).

INDUSTRIAL APPLICABILITY

A cell-penetrating peptide of the present disclosure can be usefully used in delivering a biologically active substance such as a protein, a genetic material, a chemical compound, etc. which may be used for a therapeutic purpose into cells.

The invention claimed is:

1. A fusion product comprising:
    a cell-penetrating peptide having a sequence of $(X1)_n$-X2-(cysteine)-$(X3)_m$, wherein n is an integer from 3 to 14, m is an integer from 4 to 14, each of X1 and X3 is independently arginine, lysine or histidine, and X2 is alanine, glycine, proline, tryptophan, phenylalanine, leucine, isoleucine, methionine, valine, arginine, lysine or histidine;
    a biologically active substance selected from the group consisting of a protein, a genetic material, a fat, a carbohydrate, or a chemical compound; and
    a fusing moiety linking the cell penetrating peptide and the biologically active substance,
    with the proviso that when the biologically active substance is derived from an amino acid sequence, the cell-penetrating peptide and the biologically active substance are derived from different amino acid sequences.

2. The fusion product according to claim 1, wherein the cell-penetrating peptide comprises 9-14 amino acids.

3. The fusion product according to claim 2, wherein each of X1 and X3 is independently arginine or lysine.

4. The fusion product according to claim 2, wherein X2 is alanine, tryptophan or arginine.

5. The fusion product according to claim 3, wherein the cell-penetrating peptide has an amino acid sequence of SEQ ID NO: 1, SEQ ID NO: 5, SEQ ID NO: 8 or SEQ ID NO: 12.

6. The fusion product according to claim 1, wherein the protein is a green fluorescent protein.

7. The fusion product according to claim 1, wherein the fusing moiety is an indirect linking group or a direct linking group.

8. The fusion product according to claim 7, wherein the indirect linking group is an expression vector.

9. The fusion product according to claim 8, wherein the expression vector is a recombinant protein.

10. The fusion product according to claim 7, wherein the direct linking group is a covalent or noncovalent bond.

11. The fusion product according to claim 1, wherein the genetic material is DNA or RNA.

12. The fusion product according to claim 1, wherein the chemical compound is selected from the group consisting of an anticancer drug, a therapeutic agent for an immune disease, an antiviral agent, an antibiotic, and a growth, development, or differentiation factor.

13. The fusion product according to claim 1, further comprising a tag sequence, marker, or reporter gene.

14. A composition comprising:
    a fusion product comprising:
        a cell-penetrating peptide having a sequence of $(X1)_n$-X2-(cysteine)-$(X3)_m$, wherein n is an integer from 3 to 14, m is an integer from 4 to 14, each of X1 and X3 is independently arginine, lysine or histidine, and X2 is alanine, glycine, proline, tryptophan, phenylalanine, leucine, isoleucine, methionine, valine, arginine, lysine or histidine;
        a biologically active substance selected from the group consisting of a protein, a genetic material, a fat, a carbohydrate, or a chemical compound; and
        a fusing moiety linking the cell penetrating peptide and the biologically active substance,
        wherein the cell-penetrating peptide and the biologically active substance are not derived from a single amino acid sequence; and
    a pharmaceutically acceptable carrier.

15. A method for delivering a biologically active substance, comprising
    a step of administering the fusion product according to claim 1 into the body or cells of a non-human mammal.

16. A method for gene therapy, comprising
    a step of administering the fusion product according to claim 1 into the body or cells of a non-human mammal.

17. The method according to claim 15, wherein the administering is by an injection.

18. The method according to claim 16, wherein the administering is by an injection.

* * * * *

SEQUENCE LISTING

<160> NUMBER OF SEQ ID NOS: 17

<210> SEQ ID NO 1
<211> LENGTH: 9
<212> TYPE: PRT
<213> ORGANISM: Artificial Sequence
<220> FEATURE:
<223> OTHER INFORMATION: Description of Artificial Sequence: Synthetic
      cell penetrating peptide

<400> SEQUENCE: 1

Arg Arg Arg Trp Cys Lys Arg Arg Arg
1               5

<210> SEQ ID NO 2
<211> LENGTH: 8
<212> TYPE: PRT
<213> ORGANISM: Artificial Sequence
<220> FEATURE:
<223> OTHER INFORMATION: Description of Artificial Sequence: Synthetic
      cell penetrating peptide

<400> SEQUENCE: 2

Arg Arg Trp Cys Lys Arg Arg Arg
1               5

<210> SEQ ID NO 3
<211> LENGTH: 8
<212> TYPE: PRT
<213> ORGANISM: Artificial Sequence
<220> FEATURE:
<223> OTHER INFORMATION: Description of Artificial Sequence: Synthetic
      cell penetrating peptide

<400> SEQUENCE: 3

Arg Arg Arg Trp Cys Lys Arg Arg
1               5

<210> SEQ ID NO 4
<211> LENGTH: 7
<212> TYPE: PRT
<213> ORGANISM: Artificial Sequence
<220> FEATURE:
<223> OTHER INFORMATION: Description of Artificial Sequence: Synthetic
      cell penetrating peptide

<400> SEQUENCE: 4

Arg Arg Trp Cys Lys Arg Arg
1               5

<210> SEQ ID NO 5
<211> LENGTH: 9
<212> TYPE: PRT
<213> ORGANISM: Artificial Sequence
<220> FEATURE:
<223> OTHER INFORMATION: Description of Artificial Sequence: Synthetic
      cell penetrating peptide

<400> SEQUENCE: 5

Arg Arg Arg Ala Cys Lys Arg Arg Arg
1               5

<210> SEQ ID NO 6
<211> LENGTH: 9
<212> TYPE: PRT
<213> ORGANISM: Artificial Sequence
<220> FEATURE:
<223> OTHER INFORMATION: Description of Artificial Sequence: Synthetic cell penetrating peptide

<400> SEQUENCE: 6

Arg Arg Arg Trp Ala Lys Arg Arg Arg
1               5

<210> SEQ ID NO 7
<211> LENGTH: 9
<212> TYPE: PRT
<213> ORGANISM: Artificial Sequence
<220> FEATURE:
<223> OTHER INFORMATION: Description of Artificial Sequence: Synthetic
      cell penetrating peptide

<400> SEQUENCE: 7

Arg Arg Arg Trp Cys Ala Arg Arg Arg
1               5

<210> SEQ ID NO 8
<211> LENGTH: 9
<212> TYPE: PRT
<213> ORGANISM: Artificial Sequence
<220> FEATURE:
<223> OTHER INFORMATION: Description of Artificial Sequence: Synthetic
      cell penetrating peptide

<400> SEQUENCE: 8

Arg Arg Arg Arg Cys Lys Arg Arg Arg
1               5

<210> SEQ ID NO 9
<211> LENGTH: 9
<212> TYPE: PRT
<213> ORGANISM: Artificial Sequence
<220> FEATURE:
<223> OTHER INFORMATION: Description of Artificial Sequence: Synthetic
      cell penetrating peptide

<400> SEQUENCE: 9

Arg Arg Arg Trp Arg Lys Arg Arg Arg
1               5

<210> SEQ ID NO 10
<211> LENGTH: 9
<212> TYPE: PRT
<213> ORGANISM: Artificial Sequence
<220> FEATURE:
<223> OTHER INFORMATION: Description of Artificial Sequence: Synthetic
      cell penetrating peptide

<400> SEQUENCE: 10

Arg Arg Arg Trp Cys Arg Arg Arg Arg
1               5

<210> SEQ ID NO 11
<211> LENGTH: 9
<212> TYPE: PRT
<213> ORGANISM: Artificial Sequence
<220> FEATURE:
<223> OTHER INFORMATION: Description of Artificial Sequence: Synthetic
      cell penetrating peptide

<400> SEQUENCE: 11

Arg Arg Arg Arg Arg Arg Arg Arg Arg
1               5

<210> SEQ ID NO 12

-continued

```
<211> LENGTH: 9
<212> TYPE: PRT
<213> ORGANISM: Artificial Sequence
<220> FEATURE:
<223> OTHER INFORMATION: Description of Artificial Sequence: Synthetic
      cell penetrating peptide

<400> SEQUENCE: 12

Arg Arg Arg Arg Cys Arg Arg Arg Arg
1               5

<210> SEQ ID NO 13
<211> LENGTH: 68
<212> TYPE: DNA
<213> ORGANISM: Artificial Sequence
<220> FEATURE:
<223> OTHER INFORMATION: Description of Artificial Sequence: Synthetic
      EGFP forward primer

<400> SEQUENCE: 13
ctagctagcc gccggcgctg gtgcaaacgc cgccggggat ccgtgagcaa gggcgaggag    60
ctgttcac                                                             68

<210> SEQ ID NO 14
<211> LENGTH: 25
<212> TYPE: DNA
<213> ORGANISM: Artificial Sequence
<220> FEATURE:
<223> OTHER INFORMATION: Description of Artificial Sequence: Synthetic
      EGFP reverse primer

<400> SEQUENCE: 14
caagctttta cttgtatagc tcgtc                                          25

<210> SEQ ID NO 15
<211> LENGTH: 11
<212> TYPE: PRT
<213> ORGANISM: Human immunodeficiency virus

<400> SEQUENCE: 15

Tyr Gly Arg Lys Lys Arg Arg Gln Arg Arg
1               5                   10

<210> SEQ ID NO 16
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 16

His His His His His His
1               5

<210> SEQ ID NO 17
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Asn Lys Arg Lys
1
```